United States Patent [19]

Greatbatch

[11] 4,050,004
[45] Sept. 20, 1977

[54] CARDIAC PACER INCLUDING CONTROLLED VOLTAGE MULTIPLIER

[75] Inventor: Wilson Greatbatch, Clarence, N.Y.

[73] Assignee: Wilson Greatbatch Ltd., Clarence, N.Y.

[21] Appl. No.: 429,527

[22] Filed: Jan. 2, 1974

Related U.S. Application Data

[63] Continuation-in-part of Ser. No. 32,942, April 29, 1970, Pat. No. 3,878,450.

[51] Int. Cl.$^2$ ............................................. H02M 7/00
[52] U.S. Cl. .................................. 363/59; 128/419 P
[58] Field of Search .......................... 128/419 P, 421; 307/110, 150; 321/2, 15, 18

[56] References Cited

U.S. PATENT DOCUMENTS

| | | | |
|---|---|---|---|
| 1,734,917 | 11/1929 | Peek | 321/15 |
| 2,905,881 | 9/1959 | Aron | 321/15 |
| 3,435,320 | 3/1969 | Lee et al. | 321/2 |
| 3,707,974 | 1/1973 | Raddi | 128/419 P |
| 3,818,304 | 6/1974 | Hursen et al. | 321/2 |

OTHER PUBLICATIONS

"Electronics," pp. 97, 98, Mar. 21, 1966.

"Electronics," p. 104, Mar. 2, 1970.

*Primary Examiner*—William M. Shoop
*Attorney, Agent, or Firm*—Christel & Bean

[57] ABSTRACT

A cardiac pacer including a controlled voltage multiplier adapted for connection to a source of voltage to be multiplied and a plurality of parallel voltage-developing branches each including a capacitor. A pair of output terminals, at least one of which is adapted to be operatively connected to a patient's heart, are connected in series with one of the capacitors whereby the path for current charging that capacitor is through the load connected to the terminals. A corresponding plurality of controlled switches are connected to corresponding ones of the capacitors, and the switches and capacitors are connected together to define a series discharge path including the pair of output terminals when the switches are operated by a trigger pulse generator. Including timing means controlling the generation of pulses for triggering the controlled switches and thereby controlling the stimulating output pulses appearing on the pacer output terminals. The cardiac pacer can include regulating means for limiting the amplitude of the output pulses.

12 Claims, 4 Drawing Figures

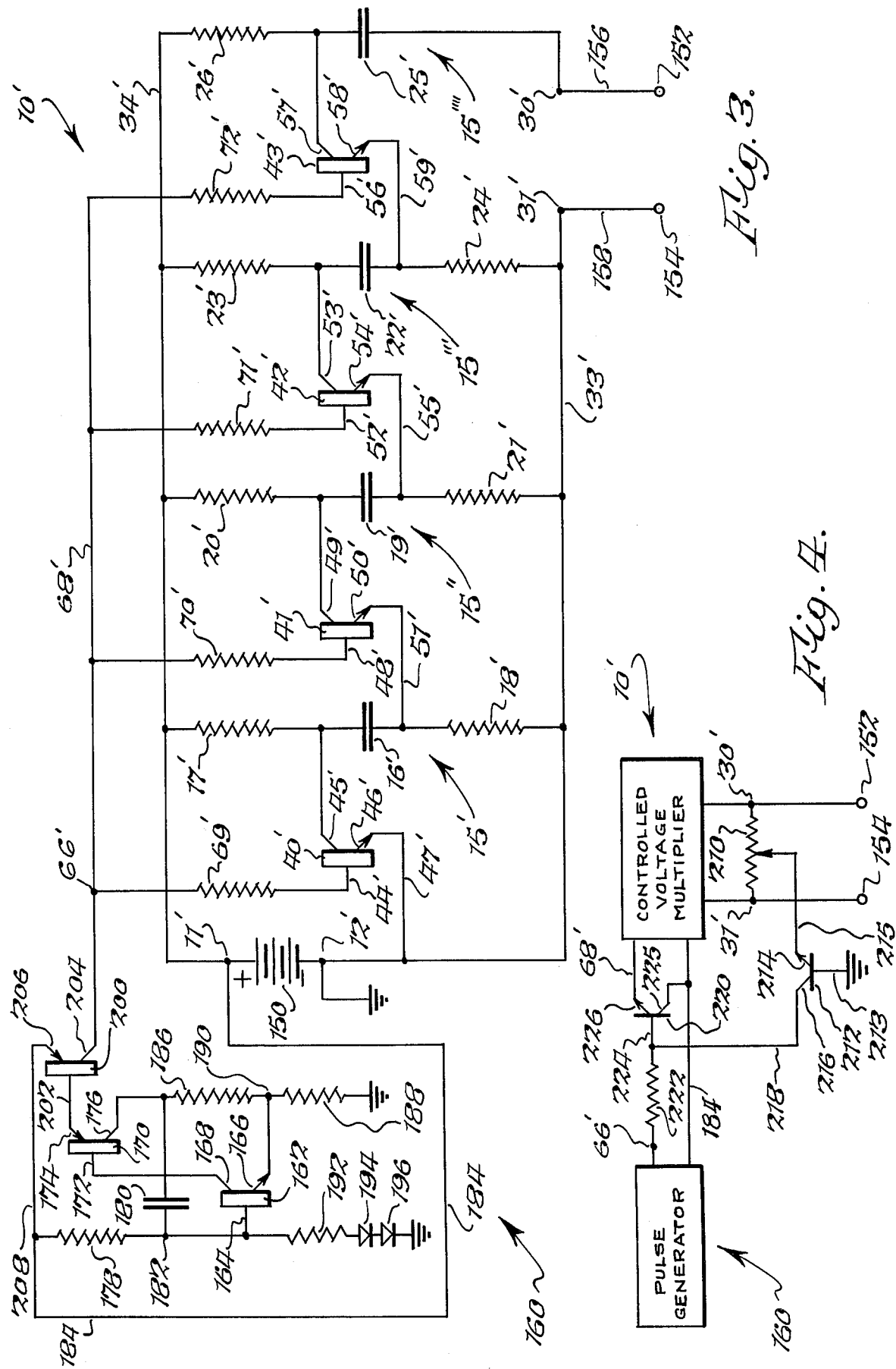

CARDIAC PACER INCLUDING CONTROLLED VOLTAGE MULTIPLIER

CROSS REFERENCE TO A RELATED APPLICATION

This application is a continuation-in-part of my pending application Ser. No. 32,942 entitled "Controlled Voltage Multiplier Providing Pulse Output" filed Apr. 29, 1970, now U.S. Pat. No. 3,878,450.

BACKGROUND OF THE INVENTION

This invention relates to the electronic cardiac pacer art and, more particularly, to a cardiac pacer including a controlled voltage multiplier for converting a low direct voltage into pulses of a relatively much larger amplitude and in a controlled manner.

Many electrical devices are powered by sources which operate at very low impedances, that is at low voltage and high current. Typical of such sources are common battery cells, which provide an output voltage of about 0.8 to 1.5 volts, human and animal nerve cells, thermoelectric, thermionic or betavoltaic generators which provide an output from about 0.1 to about 0.8 volts, as well as photocells, fuel cells and many others. Most common electronic devices or components require much higher operating voltages, for example vacuum tubes require 15 to 10,000 volts, transistors 2.5 to 250 volts and d.c. motors 1.5 to 10,000 volts.

Such an impedance mis-match is further illustrated by the specific example of an implantable artificial cardiac pacer, which requires about 2.5 volts for operation but which is powered from a rechargeable cell delivering about 0.8 volts or from a nuclear battery delivering from about 0.2 to about 0.75 volts. The low voltage of the source must be transformed into a higher voltage by a converter which is efficient, reliable and economical.

Many prior art voltage multipliers exist which operate according to the method of charging a plurality of capacitors in parallel with the available low voltage and then discharging the capacitors in series to provide a greatly increased voltage. In particular, such arrangements often employ a ladder network to isolate the power source from the high voltage discharge, and as the capacitors in the network become charged the voltage also rises across spark gaps connected in series with the capacitors. When the voltages on the gaps become sufficient, they break down placing all the capacitors in series across the load.

Such prior art arrangements are limited to relatively high operating voltages since the spark gaps in reality are voltage-actuated switches. While neon bulbs or four layer diodes might be substituted for the gaps to reduce the operating voltage to the range of tens to hundreds of volts, such arrangements nevertheless cannot be employed where it is desired to multiply fractional voltages. In addition, such arrangements have the d.c. power supply voltage appearing across the load, even during quiescent periods, and often in such arrangements the capacitors are not equally charged. Moreover, the operational requirements of an artificial cardiac pacer often render it desirable that the power supply deliver a pulsating signal having zero net average current and that all sections of the pacemaker circuit are operating at the same reference or ground potential. Voltage multipliers heretofore available, on the other hand, do not have the capability of delivering an output signal of zero net average current and, in most instances, the output thereof must float off ground.

SUMMARY OF THE INVENTION

It is, therefore, an object of this invention to provide a new and improved cardiac pacer including a voltage multiplier.

It is a further object of this invention to provide such a cardiac pacer including a voltage multiplier operable from relatively low voltage levels to provide an output voltage at zero net average current.

It is a further object of this invention to provide such a cardiac pacer including a voltage multiplier which is controlled by a pulse generator.

It is a further object of this invention to provide such a cardiac pacer including a voltage multiplier wherein all circuit portions are operating from the same reference or ground potential.

The present invention provides a cardiac pacer including a controlled voltage multiplier including a plurality of circuit branches connected in parallel with a voltage source to be multiplied and wherein each branch includes an energy storage means in the form of a capacitor. A pair of output terminals is connected to the output of the voltage multiplier, at least one of which is adapted to be operatively coupled to a patient's heart. A separate charge path is utilized for each capacitor and one charge path is also a unique discharge path, thereby permitting zero net average current through the load connected to the output terminals. A plurality of controlled switches, each connected to a corresponding energy storage means or capacitor, is provided to define a discharge path when the switches are operated by a pulse generator which includes timing means controlling the generation of pulses.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 3 is a schematic circuit diagram of a cardiac pacer including a controlled voltage multiplier according to the present invention; and FIG. 4 is a schematic circuit diagram of a cardiac pacer including a controlled voltage multiplier capable of delivering a regulated voltage output according to the present invention.

DETAILED DESCRIPTION OF THE ILLUSTRATED EMBODIMENTS

Figure 1:
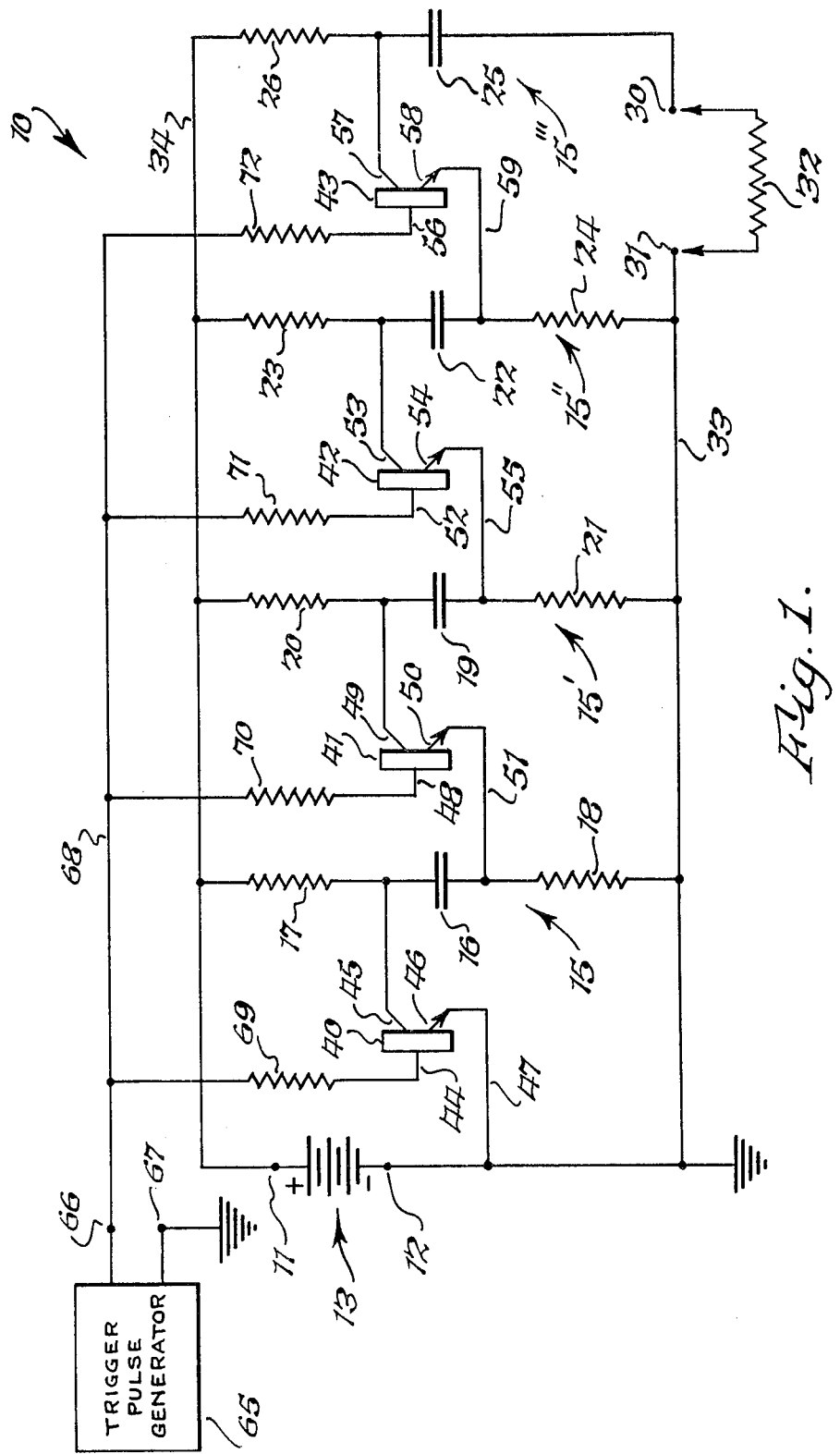
FIG. 1 is a schematic circuit diagram showing a voltage multiplier for use in the cardiac pacer according to the present invention.

FIG. 1 shows in preferred form a voltage multiplier 10 for use in the cardiac pacer of the present invention. Multiplier 10 comprises a pair of input terminals 11 and 12 adapted to be connected to a source of voltage to be multiplied. In the present instance the source to be multiplied comprises a battery indicated at 13 in FIG. 1, and advantageously battery 13 can be of the type which delivers a relatively low or fractional voltage output.

Multiplier 10 further comprises a plurality of circuit branches 15 connected electrically in parallel with input terminals 11 and 12. In the present illustration a total of four such branches are included in multiplier 10, the other three being indicated by the prime, double prime and triple prime superscripts. A small or larger number of such branches 15 can be included in multiplier 10, depending upon the amount by which it is desired to multiply the input voltage. Each branch, for example branch 15, includes energy storage means in the form of capacitor 16, together with means for developing a voltage on the branch in the form of resistors 17 and 18. Capacitor 16 is connected in series with and between resistors 17 and 18, and the series combination of capacitor 16 and resistors 17 and 18 is connected across input terminals 11 and 12. In a similar manner branch 15' includes a capacitor 19 connected in series with and between resistors 20 and 21, and the series combination of capacitor 19 and resistors 20 and 21 is connected across input terminals 11 and 12 and hence also in parallel with branch 15. Likewise, branch 15" comprises the series combination of a capacitor 22 connected between resistors 23 and 24, the entire combination being connected across input terminals 11 and 12 and hence also in parallel with branches 15 and 15'. Branch 15''' is connected across input terminals 11 and 12 and hence also in parallel with branches 15, 15' and 15", and similarly includes a capacitor 25 connected in series with a resistor 26. Field-effect transistors or other constant-current or switched devices may be substituted for the resistors in each of the branches, for example resistors 17 and 18 in branch 15.

The voltage multiplier of the present invention further comprises a pair of output terminals 30 and 31 adapted to be connected to a load which in the present illustration comprises a resistor 32. When multiplier 10 is included in an artificial cardiac pacer as will be described in detail presently, at least one of the output terminals 30, 31 is operatively coupled to a patient's heart in which case resistor 32 would represent the electrical resistance of heart and associated muscle tissue. Output terminals 30 and 31 thus are connected in series with one of the energy storage means of multiplier 10, in particular capacitor 25, whereby the path for current which charges capacitor 25 is through the load, i.e., load resistor 32. In addition, the output voltage delivered by multiplier 10 is referenced or grounded to one side of the power supply or voltage being multiplied. In particular, output terminal 31 is connected through a lead 33, together with the corresponding low voltage sides or terminals of branches 15, 15' and 15", to the relatively low or negative voltage terminal of battery 13. The relatively high voltage sides or terminals of branches 15-15''' are, of course, connected to the high or positive terminal of battery 13 through a lead 34.

Voltage multiplier 10 of the present invention further comprises a corresponding plurality of controlled switches in the form of semiconductor switching means or transistors 40-43, and each switch is connected to a corresponding one of the energy storage means or capacitors 16, 19, 22 and 25. In addition, the switches and the storage means or capacitors are connected together to define a series discharge path including output terminals 30 and 31 when the switches are operated. As shown in FIG. 1, transistor 40 has a control or base terminal 44, a collector terminal 45 connected to the junction of capacitor 16 and resistor 17 in branch 15, and an emitter terminal 46 connected by a lead 47 to input terminal 12 and, hence, the relatively low or negative terminal of battery 13. Transistor 41 has a control or base terminal 48, a collector terminal 49 connected to the junction of capacitor 19 and resistor 20 in branch 15', and an emitter terminal 50 connected by a lead 51 to the junction of capacitor 16 and resistor 18 in branch 15. Transistor 42 has a control or base terminal 52, a collector terminal 53 connected to the junction of capacitor 22 and resistor 23 in branch 15", and an emitter terminal 54 connected by a lead 55 to the junction of capacitor 19 and resistor 21 in branch 15'. Transistor 43 has a control or base terminal 56, a collector terminal 57 connected to the junction of capacitor 25 and resistor 26 in branch 15''', and an emitter terminal 58 connected by a lead 59 to the junction of capacitor 22 and resistor 24 in branch 15".

The voltage multiplier of the present invention also comprises trigger means connected to each of the switches 40-43 for operating the switches simultaneously to complete the discharge path. Referring now to FIG. 1, the trigger means comprises a pulse voltage generator indicated at 65 and having output terminals 66 and 67. According to a preferred mode of the present invention, generator 65 provides output pulses having an amplitude greater than 1 volt across terminals 66, 67. Generator 65 can be one of many forms readily available and well known to those skilled in the art and a preferred pulse generator for use with voltage multiplier 10 in an electronic cardiac pacer will be described in detail presently. Output terminal 67 of generator 65 is connected to ground, and the positive-going trigger pulses available on terminal 66 are connected through a lead 68 to transistors 40-43. In particular, lead 68 is connected through voltage-dropping resistors 69, 70, 71 and 72 to base terminals 44, 48, 52 and 56, respectively, of transistors 40-43.

Voltage multiplier 10 operates in the following manner. A voltage to be multiplied, in this particular illustration the voltage of battery 13, is connected across input terminals 11, 12. Trigger pulse generator 65 is in a quiescent state and as a result semiconductor switches or transistors 40-43 are non-conducting. The voltage to be multiplied, that of battery 13, is applied simultaneously to circuit branches 15, 15', 15", and 15''' thereby charging capacitors 16, 19, 22 and 25, respectively. Multiplier 10, therefore, provides a separate charge path for each capacitor therein.

At the time when a multiplied output voltage is desired, trigger pulse generator 65 is operated thereby providing a trigger pulse of an amplitude greater than about one volt on line 68 which is transmitted simultaneously to base or control terminals 44, 48, 52 and 56 of transistors 40, 41, 42 and 43, respectively. As a result, the transistors simultaneously are rendered conducting thereby defining a series discharge path for the capacitors through the load represented by resistor 32 connected across output terminals 30, 31. In particular, the series discharge path includes capacitors 16, 19, 22 and 25, the collector-emitter paths of transistors 40-43, line 33 and output terminals 30, 31 to which load resistor 32 is connected. Thus in response to the operation of trigger pulse generator 65 there is provided a multiplied output voltage across terminals 30, 31.

There are several advantages associated with voltage multiplier 10 constructed in accordance with the present invention. A separate charge path is provided for each of the capacitors 16, 19, 22 and 25, and one charge path, in the present instance that of branch 15''', including output terminals 30, 31, is also a unique discharge path, resulting in zero average net current through the load. This is because the charging and discharge currents are in opposite directions and is of particular significance when voltage multiplier 10 is used in conjunction with an artificial cardiac pacer. Another advantage of voltage multiplier 10 is that it is applicable to relatively low, in particular fractional, voltage systems. This is because the circuit of multiplier 10 is constructed to permit grounding of the voltage-controlled switches in such a manner that semiconductor devices such as germanium, silicon, or field-effect transistors can be employed. Such devices are low voltage in character and the only requirement is that a switching voltage of adequate amplitude, i.e., greater than about one volt, is available. A further advantage of multiplier 10 is that external control of switching time is permitted with the result that energy can be stored in capacitors 16, 19, 22 and 25 at any time, and then discharged at a high voltage upon demand rather than at random periodic intervals as in many prior art arrangements. Another advantage is that grounding of the output of multiplier 10 to one electrical side of the source to be multiplied is inherent in the circuit construction. In particular, it will be noted that when transistors 40-43 are conducting whereby the collector-emitter paths are electrically equivalent to short circuits, the discharge path from output terminal 30 through the capacitors is connected directly to the negative or relatively low voltage terminal 12 of battery 13. As a result, the output provided by multiplier 10 does not float off electrical ground as is the case with many prior art voltage multipliers. This electrical grounding of the output is of particular significance when multiplier 10 is used in conjunction with an artificial cardiac pacer wherein it is desired to have all of the circuit portions thereof operate relative to the same electrical reference potential or ground.

By way of illustration, a voltage multiplier similar to that shown at 10 in FIG. 1 but having only three branches (i.e. branches 15'-15''') was constructed wherein capacitors 19, 22 and 25 each had a value of 33 microfarads, resistors 20, 21, 23, 24, and 26 had a magnitude of 10 K, resistors 70-72 a magnitude of 22 K, and pulse generator 65 delivered trigger pulses having an amplitude of 6 volts and a duration of 1 millisecond. With the voltage of battery 13 being 6 volts, an output voltage of about 17 volts was obtained when load resistor 32 was of a magnitude of 15 K.

Figure 2:
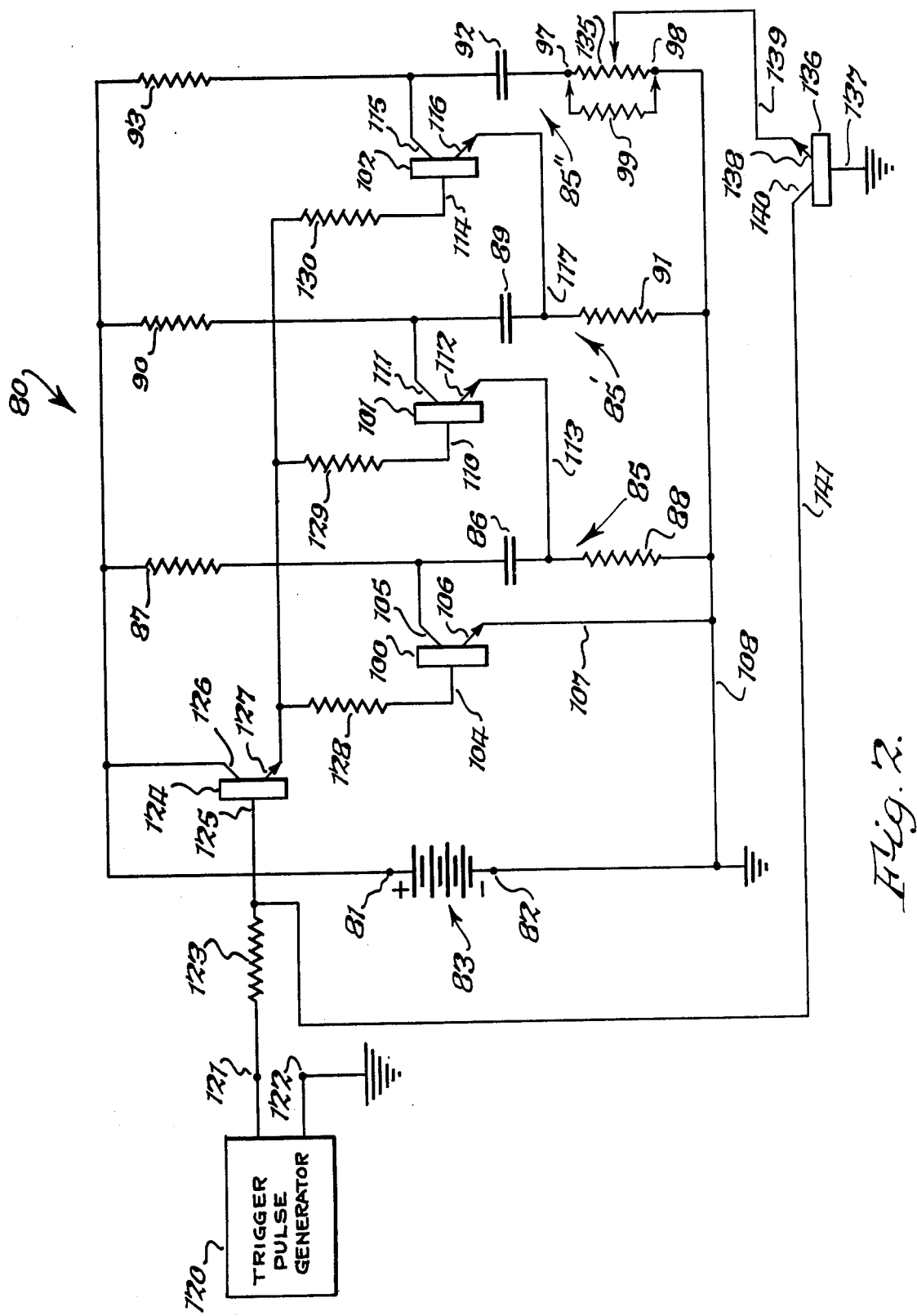
FIG. 2 is a schematic circuit diagram of a voltage multiplier capable of delivering a regulated voltage output according to the present invention.

FIG. 2 shows a voltage multiplier 80 for delivering a regulated voltage output according to the present invention. Voltage multiplier 80 includes a pair of input terminals 81 and 82 adapted for connection to a source of voltage to be multiplied, in the present instance a battery 83. Multiplier 80 further comprises a plurality of circuit branches, in the present instance three branches 85, 85' and 85", each of which branches includes energy storage means in the form of a capacitor and means for developing a voltage on the branch. In particular, branch 85 includes a capacitor 86 connected in series between resistors 87 and 88, branch 85' includes a capacitor 89 connected in series between resistors 90 and 91, and branch 85" includes a capacitor 92 connected in series with a resistor 93. Multiplier 80 further comprises a pair of output terminals 97 and 98 adapted for connection to a load 99, and the terminals are connected in series with one of the capacitors, in the present illustration capacitor 92. Load resistor 99 represents the electrical resistance of the heart when multiplier 80 is used in an artificial cardiac pacer as was the case with resistor 32 in multiplier 10.

Voltage multiplier 80 further comprises means connected to capacitors 86, 89 and 92 for defining a discharge path including output terminals 97 and 98. An arrangement similar to that of voltage multiplier 10 is provided including a corresponding plurality of semiconductor switches in the form of transistors 100, 101 and 102 each being connected to a corresponding one of the capacitors 86, 89 and 92 and the capacitors and switches being connected together to define a series discharge path including terminals 97 and 98. In particular, transistor 100 includes a control or base terminal 104, a collector terminal 105 connected to the junction of capacitor 86 and resistor 87 in branch 85, and an emitter terminal 106 connected through a lead 107 to a lead 108 which connects output terminal 98 with resistors 88 and 91 and input terminals 82. Transistor 101 includes a control or base terminal 110, a collector terminal 111 connected to the junction of capacitor 89 and resistor 90, and an emitter terminal 112 connected through a line 113 to the junction of capacitor 86 and resistor 88. Likewise, transistor 102 includes a control or base terminal 114, a collector terminal 115 connected to the junction of capacitor 92 and resistor 93, and an emitter terminal 116 connected through a lead 117 to the junction of capacitor 89 and resistor 91.

The switches or transistors 100-102 are operated simultaneously to complete the discharge path by trigger means connected to the control or base terminals thereof. In particular, a trigger pulse generator 120 having output terminals 121, 122 is included and can be of similar construction to that of pulse generator 65 shown in FIG. 1. Output terminal 122 is connected to ground and output terminal 121 is connected through a resistor 123 to a semiconductor switch in the form of transistor 124. Semiconductor switch or transistor 124 is connected in controlled relation to pulse generator 120 and in controlling relation between at least one of the input terminals of multiplier 80 and the control or base terminals of transistors or semiconductor switches 100-102. In particular, transistor 124 has a base terminal 125 connected to resistor 123, a collector terminal 126 connected to multiplier input terminal 81, and an emitter terminal 127 which is connected through resistors 128, 129 and 130 to the corresponding control or base terminals 104, 110 and 114 of transistors 100-102, respectively.

In accordance with this embodiment of the present invention, multiplier 80 includes regulating means connected to output terminals 97 and 98 and to the means defining the discharge path for stopping the flow of current through the path when the voltage on output terminals 97, 98 reaches a predetermined magnitude. In preferred form, the regulating means comprises sensing means including a variable resistance or potentiometer 135 connected between output terminals 97 and 98 and semiconductor control means in the form of transistor 136 connected in controlled relation to sensing means 135 and in controlling relation between a reference voltage and the discharge path defining means. In particular, transistor 136 has a base terminal 137 connected to a reference voltage, in the present instance electrical ground, an emitter terminal 138 is connected through a lead 139 to the wiper arm of variable resistance or potentiometer 135, and a collector terminal 140 connected through a line 141 to the junction between base terminal 125 of transistor 124 and resistor 123.

Voltage multiplier 80 operates in a manner similar to multiplier 10 of FIG. 1 to deliver a multiplied voltage output across terminals 97 and 98. In particular, the voltage to be multiplied, in the present instance the voltage of battery 83, is applied across the branches 85, 85' and 85" to charge capacitors 86, 98 and 92. When the multiplied output is desired, trigger pulse generator 120 is operated to deliver a pulse to base terminal 125 of transistor 124 to thereby render transistor 124 conducting. This in turn applies the positive voltage of battery 83 simultaneously to control or base terminals 104, 110 and 114 of transistors 100-102, respectively, thereby rendering the transistors conducting. A series discharge path thus is created including capacitors 86, 89 and 92, the collector-emitter paths of transistors 100-102, lead 108 and output terminals 97 and 98.

Characteristic of voltage multiplier 80 is the capability of providing a regulated voltage output between output terminals 97 and 98. In particular, when the voltage between terminals 97 and 98, and hence the voltage on resistance 135 exceeds the value to which resistor 135 is set, transistor 136 is driven into conduction thereby connecting base terminal 125 of transistor 124 toward ground through lead 141. This, in turn, removes the driving voltage from the control or base terminals 104, 110 and 114 of transistors 100-102, thereby opening the discharge path and limiting the output voltage to the value set by potentiometer 135.

Voltage multiplier 80 functions as a voltage regulated voltage multiplier which charges capacitors in parallel and discharges them in series with a common reference electrical ground for both the charge and discharge modes. The provision of a grounded base or grounded gate semiconductor amplifier including transistor 136 permits controlling of the negative output voltage pulse on terminals 97 and 98 without the need to provide a negative power supply. Furthermore, the grounded base or grounded gate semiconductor stage including transistor 136 functions as a dynamic variable resistance in the lower leg of a resistance voltage divider, the top leg being provided by resister 123 connected between pulse generator 120 and transistor 124.

The operation of voltage multiplier 80 is illustrated further by way of a specific example. A voltage multiplier like that of FIG. 2 was constructed with capacitors 86, 89 and 92 having a value of 33 microfarads. The resistors such as resistors 87 and 88 in each of the branches had a magnitude of 10 K and resistor 123 together with resistors 128-130 had a magnitude of 22 K. Battery 83 delivered a voltage of 6 volts, and pulse generator 120 delivered pulses having an amplitude of about 6 volts. The bottom leg of resistor 135 was variable in a range developing from about 0.55 to about 17 volts. When the bottom leg of resistor 135 was set at a value corresponding to 0.55 volts, and the voltage across terminals 97 and 98 exceeded −0.55 volts, transistor 136 was driven into conduction to ground base terminal 125 of transistor 124 thereby removing the base drive voltage from transistors 100-102. The output voltage available on terminals 97 and 98 as a result was limited to 0.55 volts or any multiple thereof as the setting of resistor 135 was changed to that corresponding to an increased voltage. Setting resistor 135 at a point corresponding to maximum voltage prevents any voltage being applied to transistor 136 with the result that full unregulated output of the multiplier is delivered to the load. With voltage multiplier 80 operating as a tripler the maximum voltage output with the top leg of resistance 135 having a maximum value of 15 K was 17 volts.

FIG. 3 is a schematic circuit diagram of a cardiac pacer including a controlled voltage multiplier according to the present invention. The controlled voltage multiplier designated 10' in the cardiac pacer of FIG. 3 is identical in construction and operation to voltage multiplier 10 of FIG. 1, and accordingly the various components thereof are designated with the same reference numerals as those in FIG. 1 but with a prime superscript. The cardiac pacer of FIG. 3 includes a voltage source in the form of a battery 150, the positive and negative terminals of which are connected to input terminals 11' and 12', respectively, of voltage multiplier 10'. Battery 150 is the type typically employed in an implantable artificial cardiac pacer.

The cardiac pacer according to the present invention further comprises a pair of pacer output terminals or electrodes 152 and 154, at least one of which is surgically placed in contact with the heart of a patient. In particular, electrode 152 would be placed surgically in contact with the ventricle of the patient's heart, and electrode 154 can function as an indifferent or reference electrode and be subcutaneously implanted in another part of the patient's body. Alternatively, electrode 154 also can be placed in contact with the patient's heart. Electrodes 152 and 154 are connected to the output of voltage multiplier 10' by leads or wires 156 and 158, respectively, which leads would be enveloped by a moisture proof and human body reaction-free material such as silicone rubber or suitable plastic. In the present instance, the output of voltage multiplier 10' is designated by the terminals 30', 31' and for purposes of illustration these terminals are connected to leads 156 and 158, respectively. It is to be understood, therefore, that electrode 152 can be connected through lead 156 directly to one terminal of capacitor 25' and likewise electrode 154 can be connected directly through lead 158 to line 33' in the circuit of FIG. 3.

The cardiac pacer of the present invention further comprises pulse generating means, designated 160, connected in controlling relation to voltage multiplier 10' and including timing means controlling the generation of pulses. Pulse generating means 160 performs a function similar to that of trigger pulse generator 65 in the circuit of FIG. 1 in that pulse generator 160 provides pulses for operating the controlled switches or transistors 40'-43' simultaneously to complete the discharge path thereby providing a multiplied output voltage across the output of voltage multiplier 10'. Pulse generating means 160 also determines or controls the pulse width or time duration together with the pulse interval or repetition rate of the stimulating pacer output pulses applied to the patient's heart. Pulse generator 160 is described in detail herein merely by way of example of a generator suitable for the cardiac pacer of the present invention. Pulse generator 160, being disclosed in U.S. Pat. No. 3,508,167, per se forms no part of the present invention, and various other pulse generators suitable for a cardiac pacer and well known to those skilled in the art can be substituted for generator 160.

Pulse generating means 160 comprises a first electronic switch in the form of an NPN transistor 162 having a control or base terminal 164, an emitter terminal 166 and a collector terminal 168. There is also included a second electronic switch in the form of PNP transistor 170 having a control or base terminal 172, an emitter terminal 174 and a collector terminal 176. Pulse generating means 160 further comprises a timing means comprising a resistor 178 serially connected to a capacitor 180. At an intermediate point 182, resistor 178 and capacitor 180 are connected to base terminal 164 of transistor 162. The other terminal of resistor 178 is connected by a line 184 to the positive terminal of battery 150. The other terminal of capacitor 180 is connected to collector terminal 176 of transistor 170.

A voltage reference in the form of a voltage divider network comprising the series combination of resistors 186 and 188 is connected between collector terminal 176 and the electrical ground or reference point for the circuit. A point 190, intermediate to resistors 186 and 188, is connected to emitter terminal 166 of transistor 162. A bypass or shunt path for operation of timing capacitor 180 includes the series combination of a resistor 192 and diodes 194, 196 connected between point 182 and the electrical ground or reference point for the circuit. The series combination of resistor 192 and capacitor 180 also comprises a timing means controlling the duration of the generation of pulses.

Pulse generating means 160 further comprises an output isolation stage in the form of a PNP transistor 200 having a control or base terminal 202, a collector terminal 204 and an emitter terminal 206. Base terminal 202 of transistor 200 is connected to emitter terminal 174 of transistor 170. Emitter terminal 206 is connected by a line 208 to line 184 and thus to the positive terminal of battery 150. Collector terminal 204 is connected to output terminal 66' of the pulse generating means 160, and terminal 66' is connected to line 68' in the circuit of voltage multiplier 10'.

Pulse generating means 160 operates in the following manner. Transistors 162, 170 and 200 initially are non-conducting and point 190 is at ground or reference potential. As soon as battery 150 is connected in the circuit, i.e., as soon as line 184 is connected to the positive terminal, capacitor 180 begins charging through resistors 178, 186 and 190. When point 182 reaches a positive voltage level large enough to forward bias the base-emitter junction of transistor 162, it begins to turn on. Marginal turn-on of transistor 162 allows sufficient base current to flow in transistor 170 to saturate it almost immediately. Saturation of transistor 170 allows base current to flow in transistor 200 thereby causing it to turn on which brings collector 204 almost to full positive voltage of the battery 150. This corresponds to the leading edge of the trigger pulse appearing at output terminal 66' and on line 68' in the voltage multiplier circuit 10'.

During the pulse, current flows from the lefthand plate of capacitor 180 as it is viewed in FIG. 3 through resistor 192 and diodes 194, 196 to the ground of reference potential point of the circuit. That current causes capacitor 180 to be charged from negative to positive proceeding from left to right plate as viewed in FIG. 3. Also during the pulse, the voltage on emitter terminal 166 of transistor 162 rises to a predetermined fraction of the voltage on resistors 186, 188 as determined by the relative magnitudes thereof.

As charge current for capacitor 180 flows in the shunt circuit, the voltage at point 182 falls toward the circuit ground or reference point. When the voltage at point 182 reaches a level less than the base-emitter voltage drop for transistor 162 above the voltage at emitter 166, transistor 162 turns off thus removing base current from transistor 170 and turning it off which, in turn, removes base current from transistor 200 thereby turning it off.

When transistor 200 cuts off, collector 204 and output terminal 66' drop immediately to the ground or reference potential thereby producing a negative-going pulse at output terminal 66'. Similarly, when transistor 170 cuts off, collector 176 drops immediately to ground potential and this drop is transmitted through capacitor 180 to base terminal 164 of transistor 162 driving it into hard cutoff by driving base terminal 164 to a potential below the ground or reference potential.

When transistors 162 and 170 turn off, capacitor 180 discharges and begins to recharge in the opposite direction as current flows from the right-hand plate as viewed in FIG. 3 through resistors 186 and 188 to the ground or reference potential for the circuit, and from the positive terminal of battery 150 through line 84 and through resistor 178 to the left-hand plate of the capacitor. Capacitor 180 charges in this direction until the potential at point 182 reaches a level or magnitude sufficient to cause turn on of transistor 162 again. The repetition rate of pulse generator 180. i.e., involving the pulse interval or time between successive or adjacent pulses, is determined by the product of the capacitance of capacitor 180 and the sum of the resistances of resistors 178, 186 and 188. Resistor 178 has a value several orders of magnitude greater than the values of resistors 186 and 188, so that the value of resistor 178 is the primary controlling resistance factor. The width or time duration of each pulse is determined primarily by the product of the resistance of resistor 192 and the capacitance of capacitor 180. According to a preferred mode of the present invention, resistor 178 has a resistance of 4 megohms, capacitor 180 has a capacitance of 0.5 microfarads, and resistors 186 and 188 have resistances of 10 K and 5 K, respectively. The value of resistor 192 is 1000 ohms. With these values for the components of pulse generating means 160 in a cardiac pacer according to the present invention, capacitor 25' in voltage multiplier 10' has a value of 10 microfarads.

The inclusion of isolation transistor 200 provides an output isolation stage for pulse generating means 160. Transistor 200 allows the circuit to operate with little effect on pulse width or pulse amplitude even when the load is short-circuited.

The cardiac pacer of the present invention can be either of the external type or implanted within the human body. To be implanted, the entire pacer including its battery which can be rechargeable is encased in an envelope of a moisture-proof and human body reaction-free material such as silicone rubber or suitable plastic so as to permit long-term implantation within the human body. U.S. Pat. No. 3,057,356 can be referred to for additional information pertaining to the structural details of an implanted pacer.

In the operation of the cardiac pacer of FIG. 3, the pulse width or time duration together with the repetition rate or pulse interval of the stimulating output pulses applied to the patient's heart from terminals 152, 154 are controlled through control of the corresponding parameters of the trigger or control pulses produced by pulse generating means 160. In particular, transistors 40'-43' are turned on to complete the series discharge path in multiplier 10' each time a trigger pulse appears on line 68'. Completion of the series discharge path initiates an output pulse across electrodes 152, 154. Thus, the time interval between successive output pulse on electrodes 152, 154 is determined by the time interval between successive trigger pulse appearing on line 68'. Expressed differently, the repetition rate or frequency of the pacer output pulses is determined by the repetition rate or frequency of pulses from generating means 160. Furthermore, the transistors 40'-43' remain conducting and hence maintain the series discharge path as long as a trigger pulse of sufficient amplitude remains on line 68'. The pulse width or time duration of each stimulating pulse appearing on output terminals 152, 154 is determined by the pulse width or time duration of each trigger pulse produced by generating means 160 and appearing on line 68'. This is because in the cardiac pacer of the present invention, the time duration of each trigger pulse produced by means 160 will be relatively short as compared to the time duration of the capacitor discharge in the series discharge path of voltage multiplier 10'.

Voltage multiplier 10' in the cardiac pacer of FIG. 3 operates in a manner similar to multiplier 10 of FIG. 1. Thus, assuming pulse generator 160 to be in a quiescent state initially, transistors 40'-43' are non-conducting and the voltage of battery 150 is applied simultaneously to circuit branches 15', 15'', 15''' and 15'''' thereby charging capacitors 16', 19', 22' and 25', respectively. At the point in time when a trigger pulse is present on line 68', as determined by the timing means in pulse generator 160, the trigger pulse is transmitted simultaneously to base or control terminals 44', 48', 52' and 56' of transistors 40', 41', 42' and 43', respectively. As a result, the transistors simultaneously are rendered conducting thereby defining a series discharge path for the capacitors through the load, i.e., the heart and associated muscle tissue of the patient. In particular, the series discharge path includes capacitors 16', 19', 22' and 25', the collector-emitter paths of transistors 40'-43', line 33' and the pacer electrodes 152 and 154, at least one of which is operatively connected to the patient's heart and which electrodes are connected by leads 156 and 158, respectively to terminals 30' and 31' in the circuit of FIG. 3. Thus in response to the operation of pulse generating means 160 producing a trigger pulse on line 68' there is provided a multiplied output voltage across electrodes 152, 154 which corresponds to the leading edge of a stimulating pacer output pulse. At the time when the trigger pulse on line 68' disappears or falls, as determined by the timing means in pulse generator 160, the voltage across electrodes 152, 154 disappears or falls corresponding to the trailing edge of that stimulating pacer output pulse. This of course occurs because transistors 40'-43' are turned off thereby opening or disconnecting the series discharge path. The foregoing events will be repeated when pulse generator 160 provides the next output pulse on line 68'. Therefore, stimulating pacer output pulses are provided across electrodes 152, 154 having a repetition rate and a pulse width or time duration as controlled by the repetition rate and width, respectively, of pulses produced by pulse generating means 160.

The cardiac pacer of the present invention includes a controlled voltage multiplier for converting a relatively low direct voltage into stimulating pacer output pulses of relatively larger amplitude and in a controlled manner. Advantageously, the low voltage is transformed into a relatively higher voltage by a converter, i.e., the voltage multiplier 10', which is efficient, reliable and economical. In particular, the provision of transistors 40'-43' make voltage multiplier 10' applicable to relatively low, such as fractional, voltage systems which is especially desirable in a cardiac pacer system. The circuit or multiplier 10' is constructed to permit grounding of the voltage-controlled switches in a manner whereby semiconductor devices such as germanium, silicon or field-effect transistors can be employed. Such devices are low voltage in character and the only requirement is that a switching voltage of adequate amplitude be available.

Another advantage of the cardiac pacer of the present invention is that the stimulating output pulses delivered by the pacer comprise a pulsating signal having zero net average current. This is of physiological and medical importance to achieve desirable results from the pacer system. A separate charge path is provided for each of the capacitors 16', 19', 22' and 25', and one charge path, which is that of branch 15'''' in FIG. 3, including the electrodes 152, 154 is also a unique discharge path, resulting in zero average net current through the load, i.e., the heart and associated muscle tissue of the patient. This is because the charging and discharge currents flow in opposite directions.

A further advantage is that in the cardiac pacer of the present invention all circuit portions operate from the same reference or ground potential. This is because grounding of the output of multiplier 10' to one electrical side of the source to be multiplied is inherent in the circuit construction. In particular, when transistors 40'-43' are conducting whereby the collector-emitter paths are electrically equivalent to short circuits, the discharge path from electrode 152 through the capacitors is connected directly to the negative or relatively low voltage terminal 12' of battery 150. As a result, the output provided by multiplier 10' does not float off electrical ground. This electrical grounding of the output is of particular significance in a cardiac pacer system wherein it is desired to have all of the circuit portions thereof operate relative to the same electrical reference potential or ground.

In some situations, it may be desireable to provide the cardiac pacer of FIG. 3 with regulating means operatively connected to the output of voltage multiplier 10' for limiting the amplitude of the multiplied output voltage to a predetermined maximum value. The regulating means is similar to that of FIG. 2, and the incorporation of such regulating means in the cardiac pacer of the present invention is illustrated in the schematic block diagram of FIG. 4. In particular, the regulating means is connected to voltage multiplier output terminals 30' and 31', and hence to the pacer output terminals 152 and 154, and is operatively connected to the means defining the discharge path for stopping the flow of current through the path when the voltage on terminals 30', 31' and terminals 152 and 154 reaches a predetermined magnitude thereby preventing any further increase in amplitude. In preferred form, the regulating means comprises sensing means including a variable resistance or potentiometer 210 connected across terminals 30', 31' and semiconductor control means in the form of transistor 212 connected in controlled relation to sensing means 210 and in controlling relation between a reference voltage and the discharge path defining means. In particular, transistor 212 has a base terminal 213 connected to the ground or reference potential of the circuit, an emitter 214 connected through a lead 215 to the wiper arm of variable resistance or potentiometer 210, and a collector terminal 216 connected through a line 218 to the junction of the base terminal of a transistor 220 and a resistor 222 connected between the output of pulse generator 160 and the input of voltage multiplier 10' in a manner similar to resistor 123 and transistor 124 in the circuit of FIG. 2. In particular, one terminal of resistor 222 is connected to output terminal 66' of pulse generator 160, and the other terminal of resistor 160 is connected to the base terminal 224 of transistor 220. Transistor 220 has a collector terminal 225 connected to line 184 and an emitter terminal 226 connected to line 68'. Transistor 220 thus comprises semiconductor switching means in the regulating means connected in controlling relation between the pulse generating means 160 and voltage multiplier 10' and connected in controlled relation to the sensing means comprising potentiometer 210 and transistor 212.

The cardiac pacer of FIG. 4 operates in a manner similar to the pacer of FIG. 3 to provide stimulating pacer output pulses on output terminals 152, 154 controlled by the timing means of pulse generator 160. Characteristic of the cardiac pacer of FIG. 4 is the capability of providing a regulated voltage output between terminals 30', 31' and 152, 154. In particular, when the voltage between terminals 30' and 31' and, hence, the voltage on resistance 210 exceeds the value to which the potentiometer 210 is set, transistor 212 is driven into conduction thereby connecting base terminal 224 of transistor 220 to the circuit reference or ground potential through line 218. This, in turn, removes the driving voltage from the control or base terminals of the transistor switches in controlled voltage multiplier 10' thereby opening the discharge path and limiting the output voltage to the value set by potentiometer 210. In other words, the amplitude of stimulating pacer output pulses on terminals 152, 154 is limited to a predetermined maximum amplitude.

Voltage multiplier 10' in the circuit of FIG. 4 functions as a voltage regulated voltage multiplier which charges capacitors in parallel and discharges them in series with a common reference electrical ground for both the charge and discharge modes. The provision of a grounded base or grounded gate semiconductor amplifier including transistor 212 permits controlling of the negative output voltage pulse on terminals 30', 31' without the need to provide a negative power supply. Furthermore, the grounded base or grounded gate semiconductor stage including transistor 212 functions as a dynamic variable resistance in the lower leg of a resistance voltage divider, the top leg being provided by resistor 222 connected between pulse generator 160 and transistor 220.

It is therefore apparent that the present invention accomplishes its intended objects. While several specific embodiments of the present invention have been described in detail, this has been done by way of illustration without thought of limitation.

I claim:

1. A cardiac pacer comprising:
   a. a voltage source;
   b. a controlled voltage multiplier having an input connected to said voltage source and an output;
   c. pulse generating means connected in controlling relation to said voltage multiplier, said pulse generating means including timing means controlling the generation of pulses; and
   d. a pair of output terminals connected to the output of said voltage multiplier, at least one of which is adapted to be operatively coupled to a patient's heart.

2. A cardiac pacer according to claim 1, wherein said controlled voltage multiplier comprises:
   a. a plurality of circuit branches connected in parallel with said input, each of said branches including energy storage means and means developing a voltage on said branch, one of said energy storage means being connected in series with said output terminal so that the path for current charging that storage means is through a load connected to said terminals;
   b. a corresponding plurality of controlled switches, each switch connected to a corresponding one of said energy storage means, said switches and said storage means being connected together to define a series discharge path including said pair of output when said switches are operated; and
   c. means connecting said pulse generating means directly to each of said switches for operating said switches simultaneously to complete said discharge path.

3. A cardiac pacer according to claim 2, wherein said energy storage means comprises a capacitor in each branch and said means developing a voltage comprises a pair of resistors in each branch, said resistors being connected in series with said capacitor and to opposite terminals thereof.

4. A cardiac pacer according to claim 2, wherein each of said controlled switches comprises a voltage controlled switch having a control terminal connected to said pulse generating means.

5. A cardiac pacer according to claim 2, wherein each of said controlled switches comprises a transistor, the collector-emitter circuit of which is connected in said discharge path and the base terminal of which is connected to said pulse generating means.

6. A cardiac pacer according to claim 5, wherein said energy storage means comprises a capacitor in each branch, said capacitors being connected to the collector-emitter circuits of said transistors, and said means developing a voltage comprises a pair of resistors in each branch, said resistors being connected in series with said capacitor and to opposite terminals thereof.

7. A cardiac pacer according to claim 2, wherein each of said circuit branches comprises a capacitor connected in series with a resistance, said output terminals are connected in series with one of said capacitors whereby the path for current charging that capacitor is through a load connected to said output terminals and each of said controlled switches is connected to a corresponding one of said capacitors whereby said switches and said capacitors are connected together to define a series discharge path including said pair of output terminals when said switches are operated.

8. A cardiac pacer according to claim 7, wherein each of said controlled switches comprises a voltage controlled switch having a control terminal connected to said pulse generating means.

9. A cardiac pacer according to claim 8, wherein each of said voltage controlled switches comprises a transistor, the collector-emitter circuit of which is connected to said capacitors and the base terminal of which is connected to said pulse generating means.

10. A cardiac pacer according to claim 1, further including regulating means operatively connected to the output of said voltage multiplier for limiting the amplitude of the multiplied output voltage to a predetermined maximum value.

11. A cardiac pacer according to claim 10, wherein said regulating means comprises:

a. sensing means connected to the output of said voltage multiplier for providing a command signal when the voltage across said output reaches said predetermined maximum value; and
b. semiconductor switching means connected in controlling relation between said pulse generating means and said voltage multiplier and connected in controlled relation to said sensing means.

12. A cardiac pacer according to claim 11, wherein said sensing means comprises a variable resistance connected across the output of said voltage multiplier and semiconductor control means connected in controlled relation to said variable resistance and in controlling relation between a reference voltage and said first-named semiconductor switching means.

* * * * *